United States Patent [19]

Miller

[11] Patent Number: 5,350,413
[45] Date of Patent: Sep. 27, 1994

[54] TRANSCUTANEOUS ENERGY TRANSFER DEVICE

[75] Inventor: John A. Miller, Ottawa, Canada

[73] Assignee: The University of Ottawa, Ottawa, Canada

[21] Appl. No.: 734,084

[22] Filed: Jul. 22, 1991

Related U.S. Application Data

[63] Continuation-in-part of Ser. No. 541,773, Jun. 21, 1990, abandoned.

[51] Int. Cl.⁵ .............................................. A61N 1/02
[52] U.S. Cl. ...................................... 607/061; 600/16; 336/115
[58] Field of Search ............... 128/419 HT, 419 PS, 128/419 C, 419 E, 419 F, 420.5, 420.6, 804, 897–899, 930, 908; 600/13–18; 336/261, DIG. 2, 115; 607/61

[56] References Cited

U.S. PATENT DOCUMENTS

| | | | |
|---|---|---|---|
| 1,145,366 | 7/1915 | Herrold | 336/231 |
| 1,727,932 | 9/1929 | Medved | 336/231 |
| 2,686,864 | 8/1954 | Wroughton et al. | 336/231 |
| 4,038,625 | 7/1977 | Tompkins et al. | 336/DIG. 2 |
| 4,338,951 | 7/1982 | Saliga | 128/908 |
| 4,408,607 | 10/1983 | Maurer | 128/419 PS |
| 4,461,302 | 7/1984 | Phillips et al. | 128/908 |
| 4,545,368 | 10/1965 | Rand et al. | 600/013 |
| 4,665,896 | 5/1987 | LaForge | 128/419 PS |
| 4,679,560 | 7/1987 | Galbraith | 128/903 |
| 4,741,339 | 5/1988 | Harrison et al. | 128/419 PS |

FOREIGN PATENT DOCUMENTS

0241307 10/1987 European Pat. Off. ......... 128/420.6

*Primary Examiner*—William E. Kamm
*Attorney, Agent, or Firm*—Venable, Baetjer, Howard & Civiletti

[57] ABSTRACT

An improved transcutaneous energy transfer (TET) device comprises a primary winding for placement on or near a skin surface, and a secondary winding for implantation under said skin surface. A field effect transistor (FET) is arranged to switch said primary coil across an external DC power supply. A tuning capacitor is linked to said primary coil whereby said primary coil, when said FET is turned off, will resonate at its natural frequency thereby compensating for drift in component values and reducing power transfer sensitivity to component drift. In an alternative aspect of the invention, a bidirectional communications link is provided for the transfer of data across a boundary layer by infrared signals. A plurality of transmitters are arranged in a circular pattern on one side of the boundary layer, whereas a receiver is positioned within the circular pattern along the opposite side of the boundary layer.

6 Claims, 4 Drawing Sheets

TRANSCUTANEOUS ENERGY TRANSFER DEVICE

CROSS-REFERENCE TO RELATED APPLICATION

This application is a continuation-in-part of U.S. patent application Ser. No. 541,773 filed on Jun. 21, 1990, now abandoned.

BACKGROUND OF THE INVENTION

1. Field of the Invention

The present invention relates to the field of medical devices. In particular, the present invention related to power supply systems for transcutaneous energy transfer (TET) devices. Even more particularly, the present invention relates to an improvement in TET devices which simplifies such devices and improves their energy transfer efficiency.

2. Description of the Related Art

A TET device is a device for providing electrical power to an implanted mechanical or electrical medical device, such as prosthetic hearts and ventricular assist devices, without having to breach the skin to lead conducting wires therethrough.

An example of a TET device is shown in U.S. Pat. No. 4,665,896 (LaForge et al) dated May 19, 1987. That patent shows a blood pump system powered by a TET device having an external primary winding and an implanted secondary winding. It is designed to be regulated to a precise degree, the power delivered to an implanted medical device. However, it is not concerned with power transfer efficiency across the skin.

U.S. Pat. No. 4,408,607 (Maurer) dated Oct. 11, 1983, on the other hand, describes a TET device which charges an implanted capacitor. Power is then drawn by a implanted medical device from the capacitor. Maurer does not require particularly efficient TET efficiency, it will be understood, because it utilizes TET technology to provide an induced voltage to charge a capacitor. An efficient capacitor is, under Maurer's proposal, much more crucial than efficient TET. Moreover, the Maurer patent relates to very small power levels-on the order of those obtainable with a fairly small implanted capacitor. With Maurer's parallel tuned circuit, Q will fall at high loads levels.

In U.S. Pat. No. 4,741,339 of May 3, 1988, Harrison et al describe a TET with improved coupling between internal and external inductive coils. The means for achieving such improved coupling proposed by Harrison includes a circuit electrically coupled to the primary coil, tuned to increase the quality factor of the primary transmitter circuit which includes the primary coil. Harrison, as well is concerned with very low power levels, and accordingly, does not have application to a system designed to provide a power source for an artificial heart.

BRIEF DESCRIPTION OF THE DRAWINGS

The object of the present invention is to provide a simple means of increasing power transmission efficiency levels in a TET device to over 80%—higher than in previous TET devices. The present invention accomplishes this result without the need for complex and expensive additional circuitry.

In one broad aspect, the present invention relates to an improved transcutaneous energy transfer (TET) device comprising: (i) a primary winding for placement at a skin surface, said primary winding being electrically connectable to an external DC power source; (ii) a secondary winding for implantation under said skin surface, coupled with said primary winding to define a transcutaneous transformer; (iii) a field effect transistor (FET) arranged in series with said primary winding to switch said primary winding across said external DC power supply for a predetermined period of time; and (iv) a tuning capacitor linked to said primary winding parallel to said FET whereby said primary winding, when said FET is turned off after said predetermined period, will resonate at its natural frequency obviating the effect of component drift in values of other electronic components of the TET device.

In another broad aspect, the present invention relates to a bidirectional communications link for the transfer of data across a boundary layer by means of infrared (IR) signal transmission and reception, said link including at least one IR transmitter on one side of boundary layer, and at least one IR receiver on the other side of said boundary layer, the improvement that comprises providing at lesat three said transmitters on one side of said boundary layer, arranged in a circular pattern, opposite said receiver on the other side of said boundary layer, said receiver being substantially at the centre of said circular pattern.

Figure 1A:
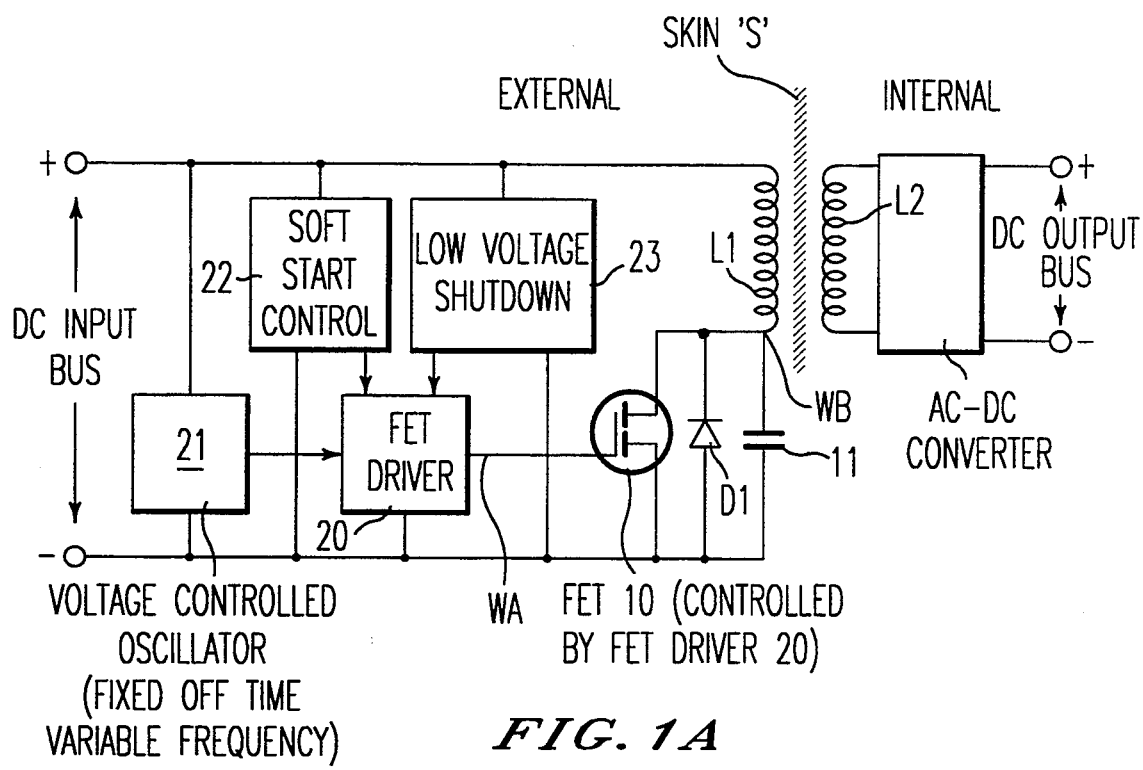
Figure 1B:
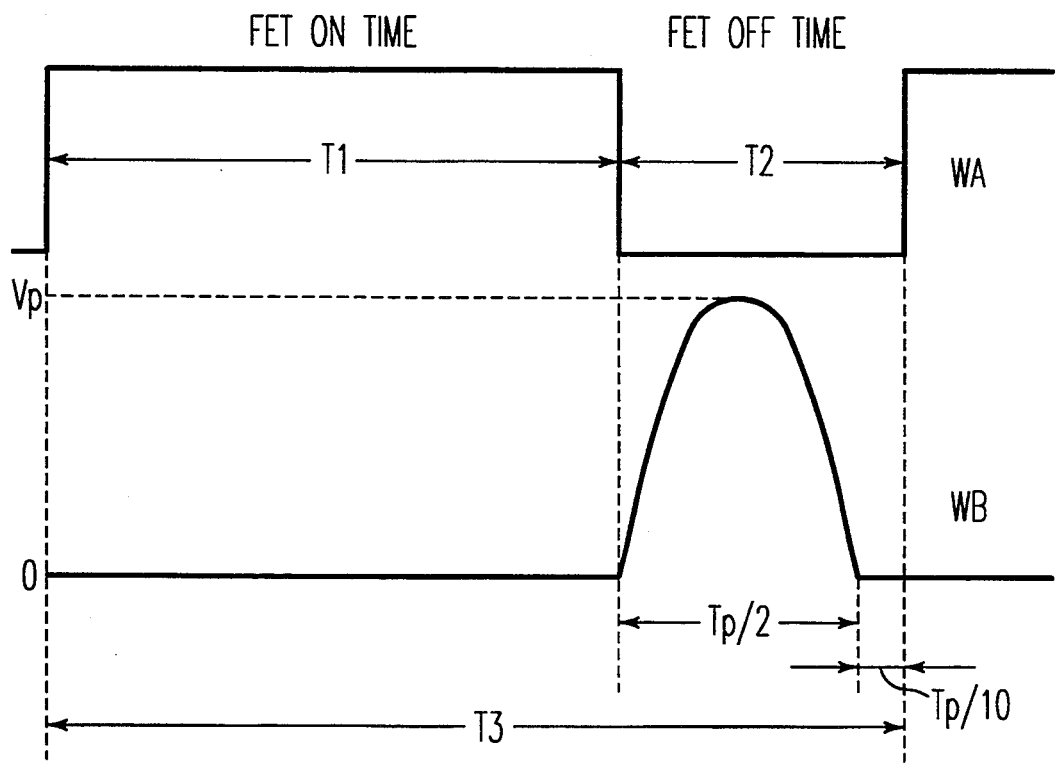
Figure 2:
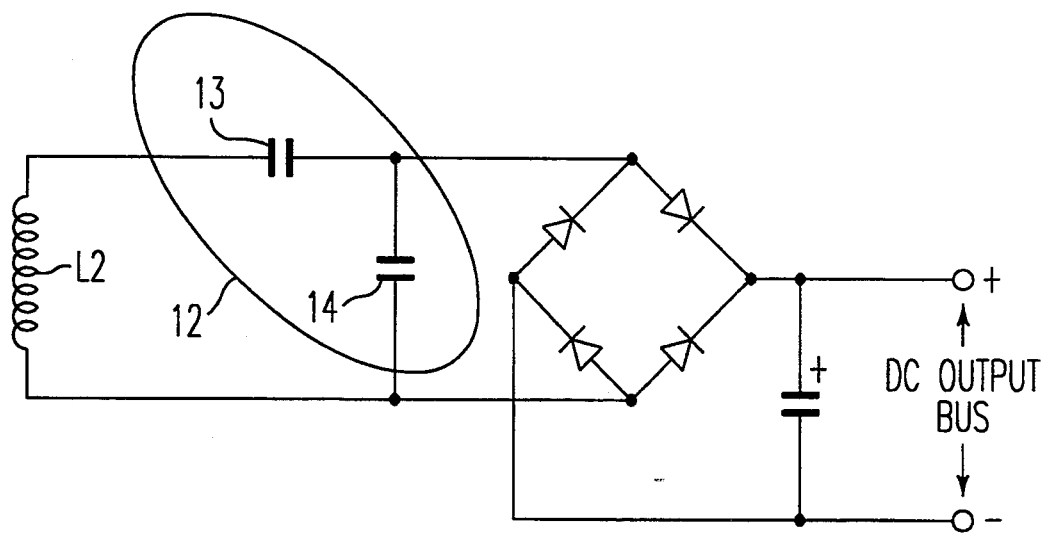
Figure 3:
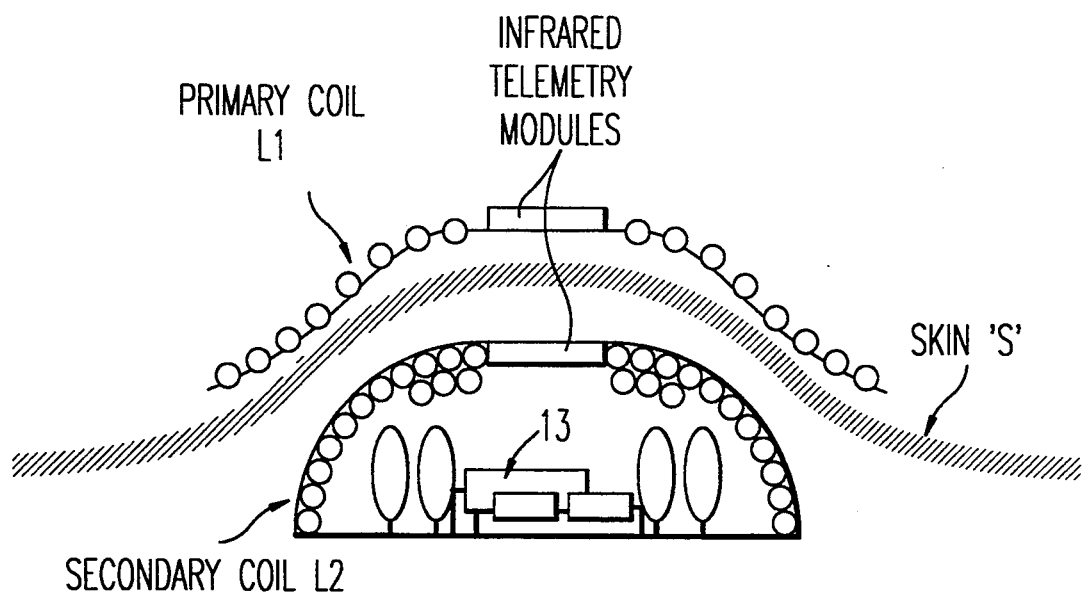
Figure 4:
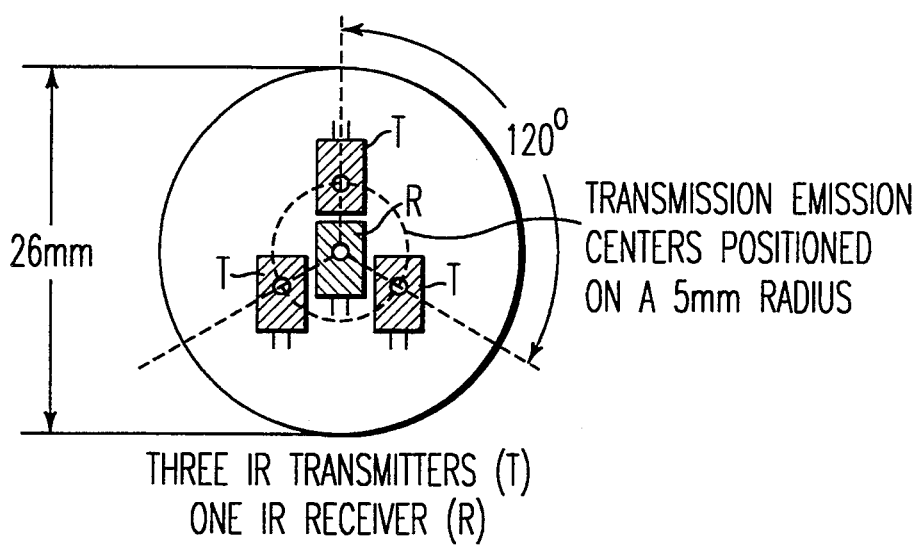
Figure 5:
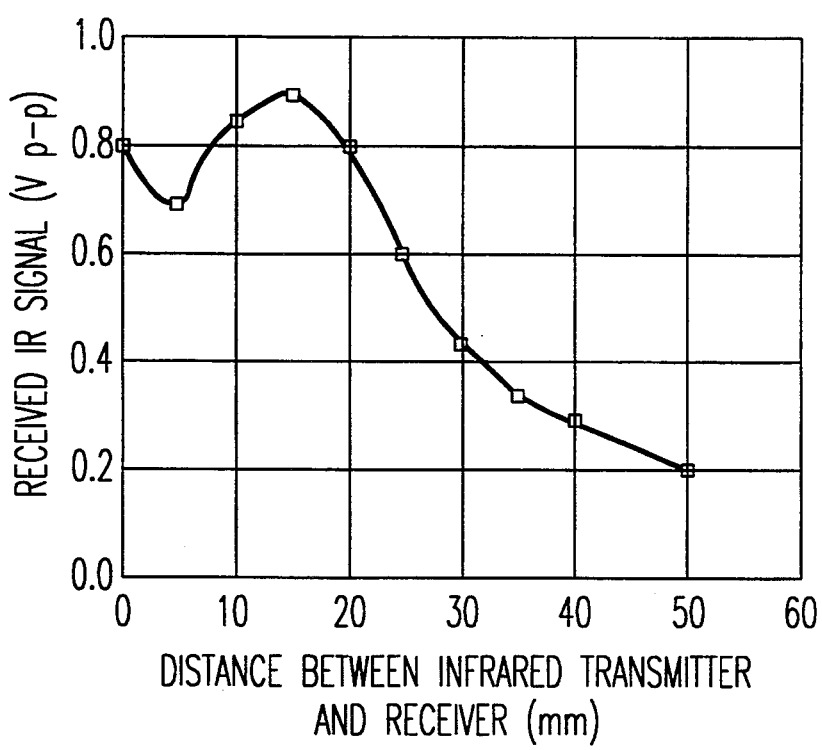
Figure 6:
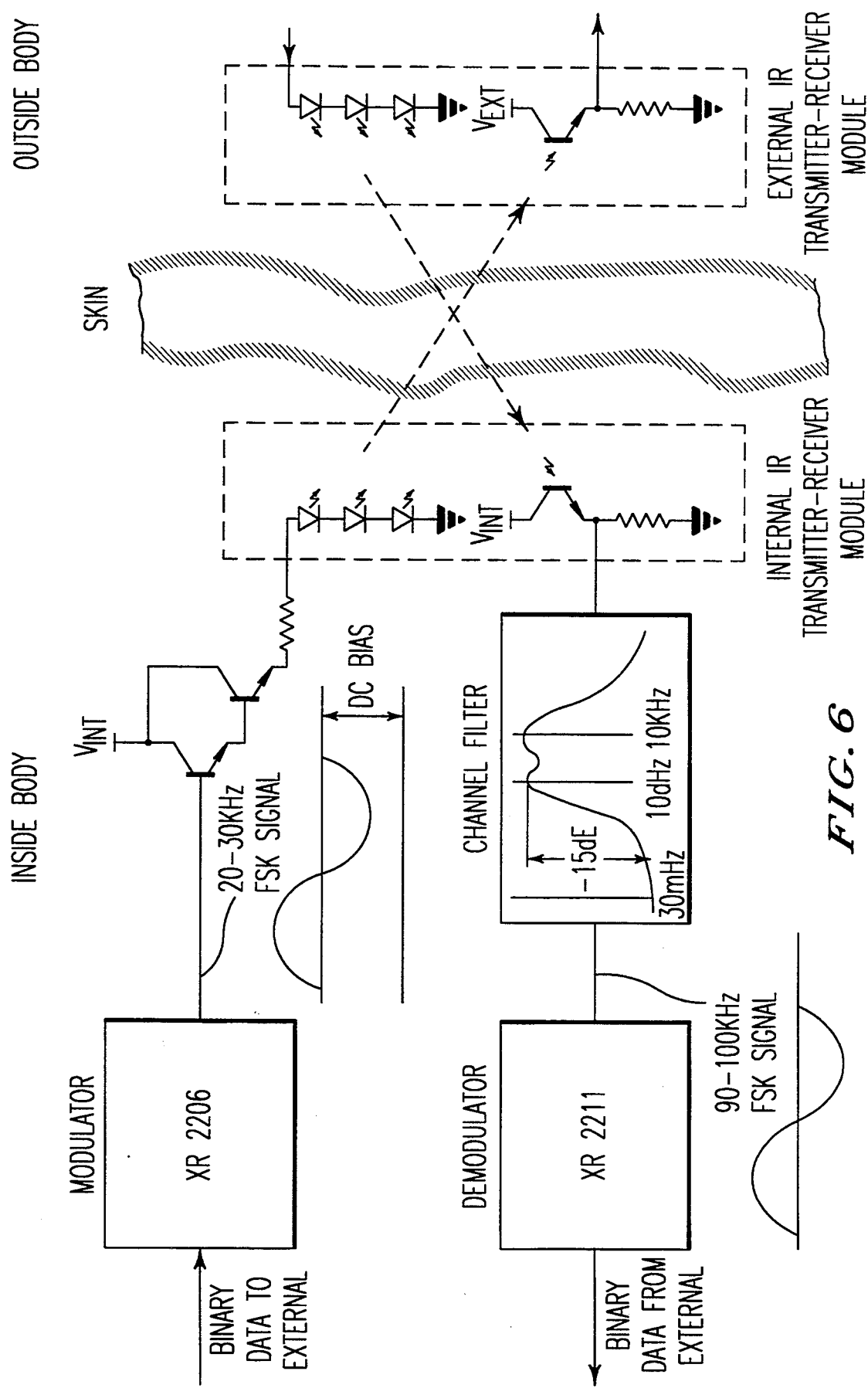

In drawings which illustrate the present invention by way of example:

FIG. 1A is a schematic of the transcutaneous energy transfer (TET) device of the present invention;

FIG. 1B is a waveform diagram comparing the voltage controlled oscillator waveform (WA) and the TET transformer excitation waveform (WB);

FIG. 2 is a detail in schematic form of the circuit of the implanted portion of the TET device shown in FIG. 1;

FIG. 3 is a cross sectional schematic of the configuration of the primary and secondary coils according to the present invention;

FIG. 4 is a schematic representation of the arrangement of infrared (IR) components in the internal and external modules;

FIG. 5 is a graph plotting received IR signal against the distance between the transmitter and the receiver; and FIG. 6 is a simplified block diagram of the IR telemetry system employed in the present invention.

DETAILED DESCRIPTION OF THE PREFERRED EMBODIMENTS

Referring now to FIGS. 1 and 2, it will first be appreciated that the present invention is a transformer designed to induce A.C. current in a subcutaneous winding, for transformation to DC to power of a medical device. AC current is induced in L2, the secondary winding which may be, for instance, a torus core, wound with Litzendraht (Litz) wire implanted just under the skin S with electrical leads connected to a medical device requiring electrical power. A similar primary winding L1 is located in alignment with the secondary winding, on the skin surface.

Primary winding L1 is connected to a capacitor 11 that is connected to the negative of a DC input bus. Winding L1 is also connected to a field effect transistor (FET) 10, as indicated in FIG. 1A. FET 10 is controlled by FET driver 20, said shown in FIG. 1A. Driver 20 receives inputs from voltage controlled oscillator 21, soft start control 22 and low voltage shutdown 23, also as shown in FIG. 1A, to produce waveform WA shown in FIGS. 1A and 1B.

Power transfer may be considered to take place in two phases, a storage phase and a resonant phase. During the storage phase, energy is stored in the primary coil using a field effect transistor (FET) to switch the coil directly across the DC input supply. The FET is selected for its very low "on" resistance to minimize the conduction losses.

In FIGS. 1A and 1B, the FET 10 is driven by a waveform WA which is generated by the voltage controlled oscillator. The period T1 represents the time when the FET 10 is turned on (on time). During this time the primary coil L1 is connected directly across the DC input power bus causing the current in L1 to rise as a linear function of time. At the end of T1 (beginning of T2) the FET 10 is turned off allowing L1 to resonate with capacitor 11. The period T2 is adjusted so that L1 when resonating with capacitor 11 is allowed to complete one half cycle of oscillation plus about 10 percent of its cycle time, i.e. T2 is approximately $Tp/2 + Tp/10$ as shown in FIG. 1B, as the short gap following $Tp/2$. The diode D1 prevents the waveform WB from going negative during the time period $T2 - Tp/2$, as illustrated in FIG. 1B.

The peak voltage Vp across the primary coil L1 is determined by the peak current attained at the end of T1, and the impedance of L1 at the circuit resonant frequency. T1 and T2 do not have a fixed relationship, their ratio will depend upon the required Vp to achieve the desired voltage transfer ratio from DC in to DC out. The primary coil L1 is turned to a frequency slightly greater than 2/T2. Some variation in the turned frequency can be tolerated providing $Tp/2 \leq T2$ and $Tp/2 > (2.T2)/3$. This latter condition is somewhat load dependant but typically variations in the resonant frequency of the primary of ±10% can be tolerated. Because the TET transformer has a low coupling coefficient (<0.5) it is possible to tune the primary and secondary coils to quite different frequencies. As previously stated the primary coil is allowed to resonate at its natural frequency (as tuned by C11) while the secondary coil is turned to the VCO frequency 1/T3 where $T3 = T1 + T2$. Waveform WB (FIG. 1B) represents the TET transformer excitation waveform which is non sinusoidal and consequently harmonic rich. The secondary coil is tuned to the fundamental and will reject harmonics according to the Q factor of the secondary circuit. The secondary coil is series tuned by capacitor 13 (see FIG. 2) thus the Q factor of the secondary circuit is dependant on the load resistance. When the load resistance is high (lightly loaded) the Q is low and so harmonic rejection will be less effective. Consequently increased levels of harmonic voltages will appear across the load resistance and contribute to the DC load voltage. This is undesirable since the output DC voltage will have a strong dependence on load conditions. In order to significantly reduce this effect C14 was introduced to stabilise the Q against load variations. The load is now considered as being composed of C14 in parallel with the actual load resistance. Under no load conditions C14 comprises the entire load maintaining an acceptable Q and preventing excessive voltages reaching the DC output. Thus C14 acts as a Q stabiliser. A low loss silver-mica capacitor has been employed to minimise $I^2R$ losses and maintain a high power transfer efficiency at all power levels from 5 to 50 watts delivered power. The implanted portion of the TET of the present invention, including the secondary coil has a duty cycle of about 0.75, and the resonant frequency of the secondary coil is lower than that of the external portion, including the primary coil L1. This arrangement results in what shall hereinafter be referred to as "dual resonance".

The resonant phase is terminated when the voltage across the FET reaches zero. At this point, the FET is again turned on to begin a new energy storage phase. Since the FET is only turned on close to a zero voltage crossing, switching losses in the FET are minimized. This enables the TET operating frequency to be increased over previous designs. Operating at higher frequencies permits smaller capacitors to be used for energy storage and smaller magnetic components for the transformer.

In addition, the use of a single ended quasi-resonant drive for the primary coil enables this circuit to tolerate variations in the transformer coupling due to coil separation. In previous designs, the primary transformer current increased as coupling was reduced, theoretically approaching infinity as the coupling reached zero. Thus it was necessary to include special circuitry to turn off the primary coil driver under such conditions. This additional circuitry is not required in the present design since a constant maximum stored energy operating mode is employed.

This mode of operation also allows the TET to tolerate induction losses due to adjacent conducting masses. In previous designs, the TET would shut down under such conditions, ceasing power transfer. The present design copes with this situation by reducing power transfer efficiency, shutting down only in extreme situations.

The use of the Litz wire contributes to the overall efficiency of the TET, which is over 80% for a wide range of load conditions. The Litz wire is composed of many individually insulated strands which are bunched in a particular way to reduce eddy current losses. There are five bunches of five bunches of three bunches of 23 strands in the Litz wire giving a total of $(5 \times 5 \times 3 \times 23 =)$ 1,725 strands. The increased surface area of the Litz wire contributes to the reduction in the losses in the coils.

As can be seen in FIG. 2, the AC current is induced in secondary winding L2 which resonates with capacitor 12. The AC is converted to DC by means of a simple circuit including a complimentary resonant capacitor 14 to further enhance the transmission efficiency of the TET systems. The secondary tuned circuit is series turned with 13 to the fundamental. As a consequence of series tuning the Q of this circuit will be dependent on the loading conditions. The load resistance can be viewed as the loss element in the tuned circuit. Because the excitation waveform is non-sinusoidal it contains harmonics which will alter the effective voltage transfer ratio of the TET device (DC to DC) as the Q of the secondary circuit changes with load. The second capacitor in the secondary tuned circuit provides a reactive load to the secondary coil under light or no load conditions. Its effect is to maintain a sufficiently high Q in the secondary circuit (which would be zero under no load conditions) to reject harmonics in the power waveform. This feature stabilises the DC output on the secondary side which would become excessive under light or no load conditions.

The inclusion of this load sensitive tuning tends to stabilize the voltage transfer ratio of the TET against load variations. This is achieved by modifying the resonant frequency of the secondary circuit as the load varies. This improves load regulation, and permits operation of the secondary circuit without complex feedback regulation.

Turning to FIG. 3, the configuration of the primary and secondary coils is illustrated. It will be understood in previous TET designs, the implanted secondary coil is substantially encircled by the torus-like primary coil which sits on the skin surface. This arrangement permits fairly accurate emplacement of the primary coil over the secondary, and means that there is very little change in coupling co-efficient if the primary and secondary coils are moved slightly, as can easily happen in normal use. The problem with this type of arrangement is that it is very sensitive to inductive influences, and the proximity of a large metal object will result in a complete shutdown of energy transfer.

The present invention however, provides a coil configuration that is relatively insensitive (about 12% power loss) to the presence of metallic objects. As can be seen from FIG. 3, the present transformer employs a primary coil having a shallow bell shaped profile which covers the secondary coil. This results in a design which is relatively insensitive to inductive interference by adjacent conducting objects. The present method of electronic power transfer is also more tolerant to inductive interference and thus the overall TET system enables the energy transfer to tolerate close contact with a metallic surface. When a large metallic plate is brought into close contact with the TET primary coil, (limited only by the insulation thickness of said primary) energy transfer efficiency falls by only about 12%. A similar situation applied to the prior systems would result in a complete shutdown of energy transfer.

The dome shaped construction of the secondary coil L2 (see FIGS. 1A, 2 and 3) assists in coupling stabilisation and also mechanical alignment of the primary coil L1 (see FIGS. 1A and 3). The internal space that this affords is utilised to house the internal AC-DC converter 13, which results in a number of significant advantages: (1) Power dissipation in the AC-DC converter is better distributed by the large copper mass of the secondary coil. (2) This power no longer contributes to the increased temperature of the internal electronic controller. (3) High frequency, high voltage AC induced in the secondary coil and transmitted directly to the AC/DC converter is kept within the secondary coil, physically isolated from sensitive electronics that may also be implanted. (4) The interconnecting wires from the AC-DC converter corrected to the secondary coil (see FIG. 1A) to the electronics and pump module of an implanted artificial heart (not illustrated) carry DC and are not part of the tuned secondary circuit. This reduces the effect on the resistance of the DC circuit and thereby increases the efficiency of the effective tuned secondary coil circuit and enables conventional smaller gauge stranded wire (not Litz) to be used to carry the DC from the coil to the electronics.

In a typical embodiment, the primary coil will be about 90 mm in diameter, with a depth of 23 mm, and the secondary coil will be 66 mm in diameter, with a depth of 24 mm.

The mechanical design of the power transfer coils allows the placement of an infrared data communications module in the top centre of each coil (see FIG. 3).

The infrared components for the internal module are mounted on small circular circuit card coaxially positioned within the internal power coil. The external IR components are similarly mounted within the primary coil.

Since a bidirectional communication link across the skin was required, the best arrangement of transmitter and receiver was investigated. FIG. 4 shows the chosen arrangement of IR components on each circular card.

Each photo-receiver is placed coaxially within a triad of diode emitters. The emission centres of the three transmitters are placed with a 120° separation on a 5 mm diameter circle centred on the receiver active point. This arrangement provides a symmetrical radiation pattern around the receiver and increases the tolerance of the IR link to coil misalignment by enlarging the radiation pattern. The diode transmitters are connected in series resulting in virtually no increase in the power demand from the supply. A further advantage of this arrangement is evident in the transmission loss versus transmitter-receiver separation. FIG. 5 shows the stabilisation effect on the IR transmission curve as the emitters and receiver are separated in air. For separations less than 5 mm the receiver is lying between the opposing transmitters, receiving IR at an oblique angle. As the separation increases a minimum is reached at about 5 mm. The location of this minimum is related to the radiant intensity pattern of the chosen transmitters. Beyond this the received signal rises as the intensity distributions of the three transmitter diodes merge. A peak in the received signal occurs at about 15 mm and then decays as the transmitter diodes begin to appear as a single point source. The thickness of the covering skin is expected to lie in the range of 5 mm to 15 mm.

The system operates at 9600 band in full duplex with an overall character error count of $<10^{-6}$. The mean current drive to the diodes is approximately 20 mA. The system is insensitive to noise from transient currents of 3 Amperes flowing in the adjacent power transfer coils. An IR transmitter-receiver axial separation of up to 150 mm can be tolerated in air without a significant increase in data errors. This is sufficient for transmission through a skin layer of 5 mm to 15 mm. Porcine skin was found to have an effective attenuation of 6–10 dB in comparison to the same separation in air. Fresh cadaver skin was found to have an attenuation in the range 6–20 dB for skin thickness of 5–15 mm.

A simplified block diagram of the full duplex FSK system is illustrated in FIG. 6. Each half of the system is composed of a single chip modulator, a single chip demodulator and a single chip active filter. Binary data from the internal processor is frequency shift keyed between 20 kHz and 30 kHz using the XR2206 modulator manufactured by EXAR. This part was chosen because it is able to produce a low distortion sine wave output and requires a minimum of external components. The output of this chip has an adjustable DC offset which provides a forward bias current for the infrared diodes. The external FSK modulator is an identical circuit but adjusted to operate at 90 and 100 kHz.

The FSK demodulator on the internal side is an XR2211 and provides a logic level output which is directly connected to the internal processor. This chip was chosen because of its large dynamic range (10 mv to 3 v rms), and its ability to operate from a single 5 volt supply. Because of the close proximity of the IR transmitter and receiver of adjacent channels, channel crosstalk is very high. Channel separation was achieved using a two stage Chebychev filter providing an interchannel rejection of 45 dB.

It is to be understood that the examples described above are not meant to limit the scope of the present invention. It is expected that numerous variants will be obvious to the person skilled in the TET art, without any departure from the spirit of the present invention. The appended claims, properly construed, form the only limitation upon the scope of the present invention.

The embodiments of the invention in which an exclusive property or privilege is claimed are defined as follows:

1. An improved transcutaneous energy transfer (TET) device comprising:
   i) a primary winding for placement adjacent to a skin surface, said primary winding being provided with electrical connection means for connecting said primary winding to an external DC power source;
   ii) a secondary winding for implantation under said skin surface and coupled with said primary winding to define a transcutaneous transformer;
   iii) a field effect transistor (FET) arranged in series with said primary winding to switch said primary winding across said external DC power supply for a predetermined period of time;
   iv) means to turn said FET on when voltage across it reaches zero and said primary winding ceases resonating; and
   v) a tuning capacitor linked to said primary winding parallel to said FET whereby said primary winding and tuning capacitor, when said FET is turned off after said predetermined period, will resonate at their natural frequency.

2. A device as claimed in claim 1, wherein said windings are made from Litzendrant wire.

3. A device as claimed in claim 1, or 2 wherein a second tuning capacitor comprising a pair of capacitors in series is provided, linked in series with said secondary coil, to stabilize the voltage transfer ratio from the primary to the secondary coil permitting operation without feedback regulation to control for output variations with load.

4. A device as claimed in claim 1, or 2 wherein said secondary winding has a duty cycle of about 0.75, and is tuned to a frequency lower than that of the first, resulting in dual resonance of said transcutaneous transformer.

5. A transcutaneous energy transfer system comprising a transformer having a primary winding and a secondary winding, said primary winding having a generally shallow bell shape to facilitate placement on a skin surface and said secondary winding having a generally shallow bell shape complementary to the shape of said primary winding to facilitate subcutaneous implantation adjacent to said primary winding, said secondary winding being dimensioned to be received within said primary winding to allow for a substantial amount of variation in the relative positions of said primary and secondary windings while minimizing the variation in coupling between said windings.

6. A transformer as described in claim 5, wherein said primary and secondary windings are made of Litzendraht wire.

* * * * *

UNITED STATES PATENT AND TRADEMARK OFFICE
CERTIFICATE OF CORRECTION

PATENT NO. : 5,350,413
DATED : September 27, 1994
INVENTOR(S) : John A. Miller

It is certified that error appears in the above-identified patent and that said Letters Patent is hereby corrected as shown below:

Cover Page, first column, under "Filed", add

"Foreign Application Priority Data
Jan. 9, 1990    [CA]    Canada..........2,007,439"

Signed and Sealed this

Second Day of March, 1999

Attest:

Q. TODD DICKINSON

Attesting Officer      Acting Commissioner of Patents and Trademarks

US005350413B1

REEXAMINATION CERTIFICATE (3866th)

United States Patent [19]
Miller

[11] B1 5,350,413
[45] Certificate Issued Sep. 7, 1999

[54] TRANSCUTANEOUS ENERGY TRANSFER DEVICE

[75] Inventor: John A. Miller, Ottawa, Canada

[73] Assignee: Ottawa Heart Institute Research Corporation, Ottawa, Canada

Reexamination Request:
No. 90/005,161, Nov. 17, 1998

Reexamination Certificate for:
Patent No.: 5,350,413
Issued: Sep. 27, 1994
Appl. No.: 07/734,084
Filed: Jul. 22, 1991

Certificate of Correction issued Mar. 2, 1999.

Related U.S. Application Data

[63] Continuation-in-part of application No. 07/541,773, Jun. 21, 1990, abandoned.

[51] Int. Cl.$^6$ ...................................................... A61N 1/02
[52] U.S. Cl. ................................ 607/61; 336/115; 600/16
[58] Field of Search .......................... 600/13, 18; 607/61; 128/897–899, 908, 930; 336/115, 261, DIG. 2

[56] References Cited

U.S. PATENT DOCUMENTS 4,015,609   4/1977   Mensink et al. ........................ 128/419

OTHER PUBLICATIONS

"A DC/DC Resonant Power Converter For An Electric Artificial Heart" by John D. Cerny, and D.C. Jeutter, Proceeding of the 11$^{th}$ Annual International Conference of the IEEE in Medicine and Biology (1), Nov. 9–12 11 (1):154–156.

Development of an Implantable Motor–Driven Assist Pump System by Y. Mitamura, et al. IEEE Trans. Biomed. Eng. 37(2):146–156(1990).

*Primary Examiner*—William E. Kamm

[57] ABSTRACT

An improved transcutaneous energy transfer (TET) device comprises a primary winding for placement on or near a skin surface, and a secondary winding for implantation under said skin surface. A field effect transistor (FET) is arranged to switch said primary coil across an external DC power supply. A tuning capacitor is linked to said primary coil whereby said primary coil, when said FET is turned off, will resonate at its natural frequency thereby compensating for drift in component values and reducing power transfer sensitivity to component drift. In an alternative aspect of the invention, a bidirectional communications, link is provided for the transfer or data across a boundary layer by infrared signals. A plurality of transmitters are arranged in a circular pattern on one side of the boundary layer, whereas a receiver is positioned within the circular pattern along the opposite side of the boundary layer.

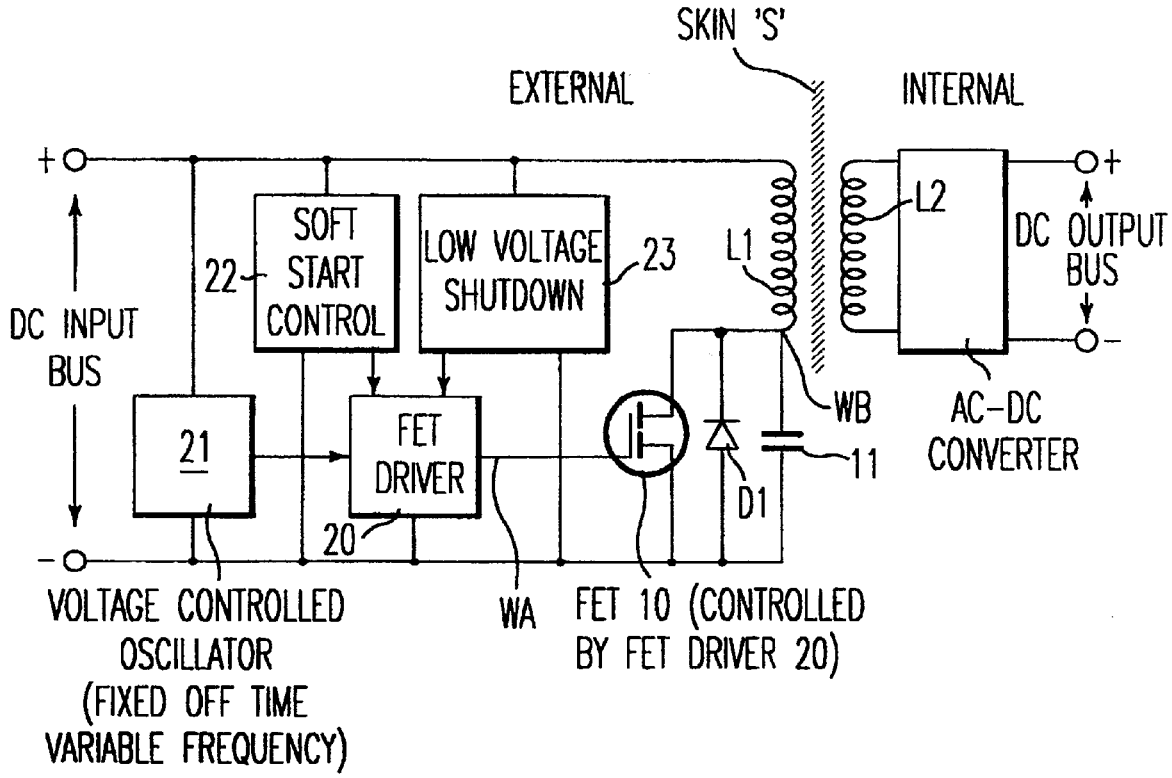

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *